United States Patent [19]
Huston et al.

[11] Patent Number: 5,976,821
[45] Date of Patent: Nov. 2, 1999

[54] MONOCLONAL ANTIBODIES SPECIFIC FOR HUMAN INTERLEUKIN-5

[75] Inventors: David P. Huston; Richard R. Dickason; Marilyn M. Huston, all of Houston, Tex.

[73] Assignee: Baylor College of Medicine, Houston, Tex.

[21] Appl. No.: 08/547,480

[22] Filed: Oct. 24, 1995

Related U.S. Application Data

[63] Continuation of application No. 08/154,402, Nov. 19, 1993, abandoned.

[51] Int. Cl.$^6$ .............. G01N 33/543; G01N 33/577; C07K 16/24; C12P 21/08
[52] U.S. Cl. .............. 435/7.94; 435/7.92; 435/70.21; 435/172.2; 435/240.27; 436/512; 436/518; 436/536; 436/548; 530/388.23; 935/104; 935/110
[58] Field of Search .................. 435/7.92, 7.93, 435/7.94, 7.95, 70.21, 172.2, 240.27; 436/518, 536, 547, 548, 512; 530/388.23, 391.3; 935/104, 110

[56] References Cited

PUBLICATIONS

Fukuda et al., 1991. A sandwich Enzyme–Linked Immunosorbent Assay for Human Interleukin–5. J. Immunol. Meth 143:89–94.

McKenzie et al., 1992. "Interleukin–5", in *Interleukins: Molecular Biology and Immunology*. (Kishimoto, ed.) Chem. Immunol. Basel, Karger vol. 51, pp. 135–152.

Goding, 1983. *Monoclonal Antibodies: Principles and Practice*. London, Academic Press, Inc. pp. 118–123.

McNamee et al., 1991. Production Characterization and Use of Monoclonal Antibodies to Human Interleukin–5 in an Enzyme–Linked Immunosorbent Assay. J Immunol. Meth. 141: 81–88.

Hellstrom et al., 1985. in *Monoclonal Antibodies for Cancer Detection and Therapy* (Baldwin et al., eds.) London, Academic Press. p. 20.

Rehfeld et al., 1983. Residue Specific Radioimmunoanalysis . . . J Biochem Biophys. Meth. 7:161–170.

*Primary Examiner*—James C. Housel
*Assistant Examiner*—James L. Grun
*Attorney, Agent, or Firm*—Fulbright & Jaworski L.L.P.

[57] ABSTRACT

Monoclonal antibodies which specifically bind to human interleukin-5 (IL-5) are described. The antibodies can be used in assays for IL-5, to purify IL-5, or to characterize IL-5.

35 Claims, 5 Drawing Sheets anti-hIL-5 mAb anti-hIL-5 mAb

MONOCLONAL ANTIBODIES SPECIFIC FOR HUMAN INTERLEUKIN-5

This is a continuation of application Ser. No. 08/154,402, filed Nov. 19, 1993, now abandoned.

FIELD OF THE INVENTION

The present invention is in the field of recombinant DNA technology. This invention is directed to antibodies, and in particular, monoclonal antibodies that are capable of specifically binding to human interleukin-5. The invention concerns the development of such antibodies, as well as their diagnostic and therapeutic uses.

BACKGROUND OF THE INVENTION

I. Interleukin-5 and the Humoral Response to Microbial Infection

Antibodies are produced by the immune system of humans and animals in response to the presence of molecules that are considered "foreign." Such molecules fall into two classes: "antigens" or "haptens." An antigen is a molecule whose presence in an animal is capable of inducing the immune system to produce antibodies. In contrast, a hapten is capable of being bound by an antibody, but is not capable of eliciting antibody formation. Haptens are generally small molecules; when conjugated to a larger molecule, they can become antigens, and thus induce antibody formation. The nature and structure of antibodies, and the tenets of immunology are disclosed by Davis, B. D. et al. (In: *Microbiology*, 2nd Ed., Harper & Row, NY (1973)).

The capacity to induce antibody formation in response to microbial infection depends upon a series of interactions among T cells, B cells, and macrophages. Each B cell is genetically programmed to produce cells that express an immunoglobulin (or antibody) that is capable of specific interaction with a distinct antigenic determinant on the infectious microbe. Such antibodies play a central role in the humoral response to infection (Takatsu, K., *Microbial Rev* 35:593–606 (1991)).

The B cell response to an antigen is regulated by a helper T cell responding to, and specific for, the same antigen molecule (Takatsu, K., *Microbial Rev* 35:593–606 (1991)). The helper T cells recognize antigenic peptides in the context of class II major histocompatability complex (MHC) molecules that are arrayed on B cells, and secrete several soluble factors ("lymphokines") which can induce growth and maturation of B cells (Howard, M. et al., *Ann. Rev. Immunol.* 1:307–333 (1983); Kishimoto, T. et al., *Ann. Rev. Immunol.* 3:133–157 (1985); Melchers, F. et al., *Ann Rev. Immunol.* 4:13–36 (1986); Takatsu, K., *Microbial Rev* 35:593–606 (1991)).

One of these soluble factors (termed, "T-cell-replacing factor" ("TRF") was found to induce the terminal differentiation of activated B cells into antibody producing cells (Takatsu, K. et al., *J. Immunol.* 124:2414–2422 (1980)). This factor was subsequently found to have an activity (termed "BCGF II") that could promote DNA synthesis in certain B cell leukemic cells (Harada, N. et al., *J. Immunol.* 134:3944–3951 (1985)). Further research revealed the additional presence of an eosinophil differentiation factor capable of inducing eosinophil colony formation (Sanderson, C. J. et al., *J. Exper. Med.* 162:60–74 (1985)). Ultimately, these factors were purified (Sanderson, C. J. et al., *Proc. Natl. Acad. Sci. (U.S.A.)* 83:437–440 (1986)) and sequenced (Campbell, H. D. et al., *Eur. J. Biochem*, 174:345–352 (1988); Kinashi, T. et al., *Nature* 324:70–73 (1986)), and found to be derived from a single protein, termed "interleukin-5" ("IL-5") (McKenzie, A. N. N. et al., In: *Interleukins: Molecular Biology and Immunology*, Chem. Immunol., Basel, Karger, vol. 51, pp 135–152 (1992), herein incorporated by reference).

The cDNA encoding murine IL-5-TRF/BCGFII was cloned by using SP6 expression vector system (Kinashi, T., et al., *Nature* 324:70–73 (1986)). The amino acid sequence deduced from the nucleotide sequence of the entire IL-5 cDNA revealed that murine IL-5 consists of 133 amino acids including a hydrophobic signal sequence of 20 amino acids (Kinashi, T., et al.,*Nature* 324:70–73 (1986)) with a molecular mass of 12.3 kDa. Thus, the mature human IL-5 protein has 113 amino acids, and is the same length as the mature murine IL-5. Comparison of the cDNA sequence of murine IL-5 with that of human shows a sequence homology of 77% at the DNA level and 70% at the protein level.

Interleukin-5 is a homodimeric glycoprotein. Investigations using reduced and alkylated IL-5 suggest that dimerization is essential for biological activity (Tsuroka, N., et al., *Cell. Immunol.* 125:354–362 (1990)). Comparison of the two polypeptide sequences shows 81 identical amino acids, 25 conservative amino acid changes, with the remaining 7 (and the two N-terminal amino acids of the human protein sequence) as non-conservative changes. This high degree of similarity is reflected in the ability of the two proteins to cross-react with cells of other mammals (Sanderson, C. J., et al., In: *Colony Stimulating Factors: Molecular and Cellular Biology*, Marcel Dekker, NY, pp 231–256 (1990)). Despite their capacity to cross react, murine and human IL-5 display significant species specificity, with the murine material being approximately 100-fold more active against murine cells than the human molecule. Conversely, human IL-5 is approximately 20-fold more active in human bone marrow assays than murine IL-5)McKenzie, A. N. J. et al., In: *Interleukins: Molecular Biology and Immunology*, Chem. Immunol., Basel, Karger, vol. 51, pp 135–152 (1992)).

Native IL-5 or recombinant IL-5 expressed in mammalian cells in heterogeneously glycosylated, with the mouse sequence containing three potential N-glycosylation sites, while the human sequence lacks on of these. Carbohydrate has been shown to be unnecessary for biological activity, although it is possible that it may perform some role in governing the half-life of the polypeptide in the circulation (McKenzie, A. N. J. et al., In: *Interleukins: Molecular Biology and Immunology*, Chem. Immunol., Basel, Karger, vol. 51, pp 135–152 (1992)).

Interleukin-5 promotes the growth of B-lineage cells. IL-5 acts on naturally activated B cells, on LPS-stimulated B cells, and on resting B cells to induce maturation and to propagate proliferation (Karasuyama, H. et al., *J. Exper. Med.* 167:1377–1390 (1988)). IL-5 induces the increase in levels of secreted forms of $\mu$-mRNA in $BCL_1$ or resting as well as activated B cells (Webb, C. P. et al. *J. Immunol.* 143:3934–3939 (1989)). Murine IL-5 was found to cause an increase in the frequency of B cells both proliferating and Ig secreting (Alderson, M. R. et al., *J. Immunol.* 139:2656–2660 (1987)). IL-5 can induce antigen-specific and polyclonal IgA production in antigen-primed B cells and in LPS-stimulating B cells, respectively.

IL-5 also appears to promote immunoglobulin formation. Transgenic mice carrying the IL-5 gene exhibited elevated levels of IL-5 in the serum (2–10 ng/ml), and an increase in the levels of serum IgM and IgA. A marked increase in the number of peripheral blood white cells (PBL), of spleen cells and of peritoneal cells was also observed. Particularly, the increase in the numbers of eosinophils in PBL reached 70-fold those of age-matched control mice (Tominaga, A. et al., *J. Exper. Med.* 144:1345–1352 (1990)). Antibodies to IL-5 mAbs have been isolated (Coffman, R. L. et al., *Science* 245:308–311 (1989)), and have been found to inhibit the antigent-specific primary IgM response induced by a cloned helper T cells in an MHC-restricted manner and also to inhibit polyclonal Ig-secretion (Rasmussen, R. et al., *J. Immunol.* 140:705–712 (1988)).

Importantly, IL-5 also plays a role in the production and maturation of eosinophils. Eosinophils are immune system cells that accumulate in response to allergic inflammatory reactions. They ingest antibody-antigen complexes and thereby become degranulated. Since the granules contain substances capable of blocking the action of histamine, serotonin and bradykinin, all of which are involved in inflammation, it has been proposed that eosinophils protect the tissues of the host not only by phagocytizing and degrading cytotoxic antibody-antigen complexes but also by damping the effects of chemical mediators of the inflammatory response (Davis, B. D. et al., In: *Microbiology*, 2nd Edit., Harper & Row, NY (1973)). IL-5 thus plays an important part in diseases associated with increased iosiniphils, such as asthma and similar inflammatory conditions (Sanderson, C. J., In: *Advances in Pharmacology*, vol. 23, Academic Press, NY, pp. 163–177 (1992); Takatsu, K., *Curr. Opin. Immunol.* 4:299–306 (1992), both herein incorporated by reference).

Murine IL-5 has also been shown to induce the production of eosinophils in liquid bone marrow cultures (McKenzie, A. N. J. et al., In: *Interleukins: Molecular Biology and Immunology*, Chem. Immunol., Basel, Karger, vol. 51, pp 135–152 (1992)). maintain the viability of mature eosinophils, to induce the production of superoxide anion in mature eosinophils and to possess chemotactic activity for eosinophils (Harada, N. et al., *J. Immunol.* 134:3944–3951 (1985); Lopez, A. F. et al., *J. Exp. Med.* 167:219–224 (1987); Owen, W. F. et al., *J. Exper. Med.* 170:343–349 (1989); Yamaguchi, N. et al., *J. Exper. Med.* 167:43–56 (1988); Yamaguchi, N. et al., *J. Exper. Med.* 167:1737–1742 (1988)). The syngergistic effect of IL-5 and colony-stimulating factors on the expansion of eosinophils is supposed to contribute to the urgent mobilization of eosinophils at the time of helminthic infections and allergic responses.

Thus, IL-5 appears to play a significant role in inducing inflammatory processes. Molecules that potentiate this activity are therefore highly desired anti-inflammatory agents.

II. Antibodies and Immunoassays

Immunoassays are assay systems that exploit the ability of an antibody to specifically recognize and bind to a particular target molecule. Immunoassays are used extensively in modern diagnostics (Fackrell, *J. Clin. Immunoassay* 8:213–219 (1985)). A large number of different immunoassay formats have been described (Yolken, R. H., *Rev. Infect. Dis.* 4:35 (1982); Collins, W. P., In: *Alternative Immunoassays, John Wiley & Sons, NY* (1985); Ngo, T. T. et al., In: *Enzyme Mediated Immunoassay*, Plenum Press, NY (1985)).

The simplest immunoassay involves merely incubating an antibody that is capable of binding to a predetermined target molecule with a sample suspected to contain the target molecule. The presence of the target molecule is determined by the presence, and proportional to the concentration, of any antibody bound to the target molecule. In order to facilitate the separation of target-bound antibody from the unbound antibody initially present, a solid phase is typically employed. Thus, for example the sample can be passively bound to a solid support, and, after incubation with the antibody, the support can be washed to remove any unbound antibody.

In more sophisticated immunoassays, the concentration of the target molecule is determined by binding the antibody to a support, and then permitting the support to be in contact with a sample suspected to contain the target molecule. Target molecules that have become bound to the immobilized antibody can be detected in any of a variety of ways. For example, the support can be incubated in the presence of a labelled, second antibody that is capable of binding to a second epitope of the target molecule. Immobilization of the labelled antibody on the support thus requires the presence of the target, and is proportional to the concentration of the target in the sample. In an alternative assay, the target is incubated with the sample and with a known amount of labelled target. The presence of any target molecules in the sample competes with the labelled target molecules for antibody binding sites. Thus, the amount of labelled target molecules that are able to bind the antibody is inversely proportional to the concentration of target molecule in the sample.

In general, immunoassay formats employ either radioactive labels ("RIAs") or enzyme labels ("ELISAs"). RIAs have the advantages of simplicity, sensitivity, and ease of use. Radioactive labels are of relatively small atomic dimension, and do not normally affect reaction kinetics. Such assays suffer, however, from the disadvantages that, due to radioisotopic decay, the reagents have a short shelf-life, require special handling and disposal, and entail the use of complex and expensive analytical equipment. RIAs are described in *Laboratory Techniques and Biochemistry in Molecular Biology*, by Work, T. S., et al., North Holland Publishing Company, NY (1978), with particular reference to the chapter entitled "An Introduction to Radioimmune Assay and Related Techniques" by Chard, T., incorporated by reference herein.

ELISAs have the advantage that they can be conducted using inexpensive equipment, and with a myriad of different enzymes, such that a large number of detection strategies—colorimetric, pH, gas evolution, etc.—can be used to quantitate the assay. In addition, the enzyme reagents have relatively long shelf-lives, and lack the risk of radiation contamination that attends to RIA use. ELISAs are described in *ELISA and Other Solid Phase Immunoassays* (Kemeny, D. M. et al., Eds.), John Wiley & Sons, NY (1988), incorporated by reference herein.

Antibodies that would be capable of specific binding to Interleukin-5 would be highly desired aids in detecting or quantifying IL-5 presence or levels. Although antibodies to the murine IL-5 have been identified that also bind human IL-5, it would be desirable to have antibodies of greater specificity and/or avidity to human IL-5. Such reagents would also be valuable in determining IL-5 derivatives and mimetics having increased or modified biological activity. The present invention provides such antibodies, as well as methods for their exploitation.

SUMMARY OF THE INVENTION

The present invention concerns antibodies, and in particular, monoclonal antibodies that are capable of specifically binding to human interleukin-5. The invention provides methods for forming such molecules, and for using such molecules to measure IL-5 levels in a sample, as well as to design potential IL-5 therapeutics. Although the invention particularly concerns murine monoclonal antibodies, it is also directed to the development of IL-5 ligands, and to humanized antibodies.

In detail, the invention concerns an antibody, or fragment thereof, capable of specifically binding human interleukin-5, wherein the antibody or protein is substantially incapable of binding murine interleukin-5.

The invention also concerns a cell (mammalian, insect, bacterial, etc.) capable of producing an antibody, or fragment thereof, that is capable of specifically binding human interleukin-5, wherein the antibody or protein is substantially incapable of binding murine interleukin-5.

The invention also concerns a baculovirus vector capable of directing the expression of human IL-5 in an insect cell, as well as the insect cell that contains such vector.

The invention provides a method for determining whether a candidate agent is capable of modulating a biological activity of human interleukin-5, which comprises incubating the candidate agent in the presence of an antibody, or fragment thereof, capable of specifically binding human interleukin-5, but substantially incapable of binding murine interleukin-5, and determining whether the agent is capable of being bound by the antibody or fragment.

The invention further provides a method for determining the presence or concentration of interleukin-5 in a sample which comprises contacting the sample with an antibody, or fragment thereof, capable of specifically binding human interleukin-5, but substantially incapable of binding murine interleukin-5, and determining whether the sample contains a molecule capable of binding to the antibody or fragment.

BRIEF DESCRIPTION OF THE FIGURES

FIG. 3A: Nonreduced rhIL-5 was electrophoresed and transferred to PVDF membrane. Each number represent the respective anti-hIL-5 primary mAb incubated at 100 μg/ml. The (–) lane was run without primary mAb. FIG. 3B: Conditions were the same as above except rhIL-5 was run under reducing conditions in all lanes except (+) which was a positive control for Western development and contained nonreduced rhIL-5 detected with IL5.5.

DETAILED DESCRIPTION OF THE INVENTION

Figure 1:
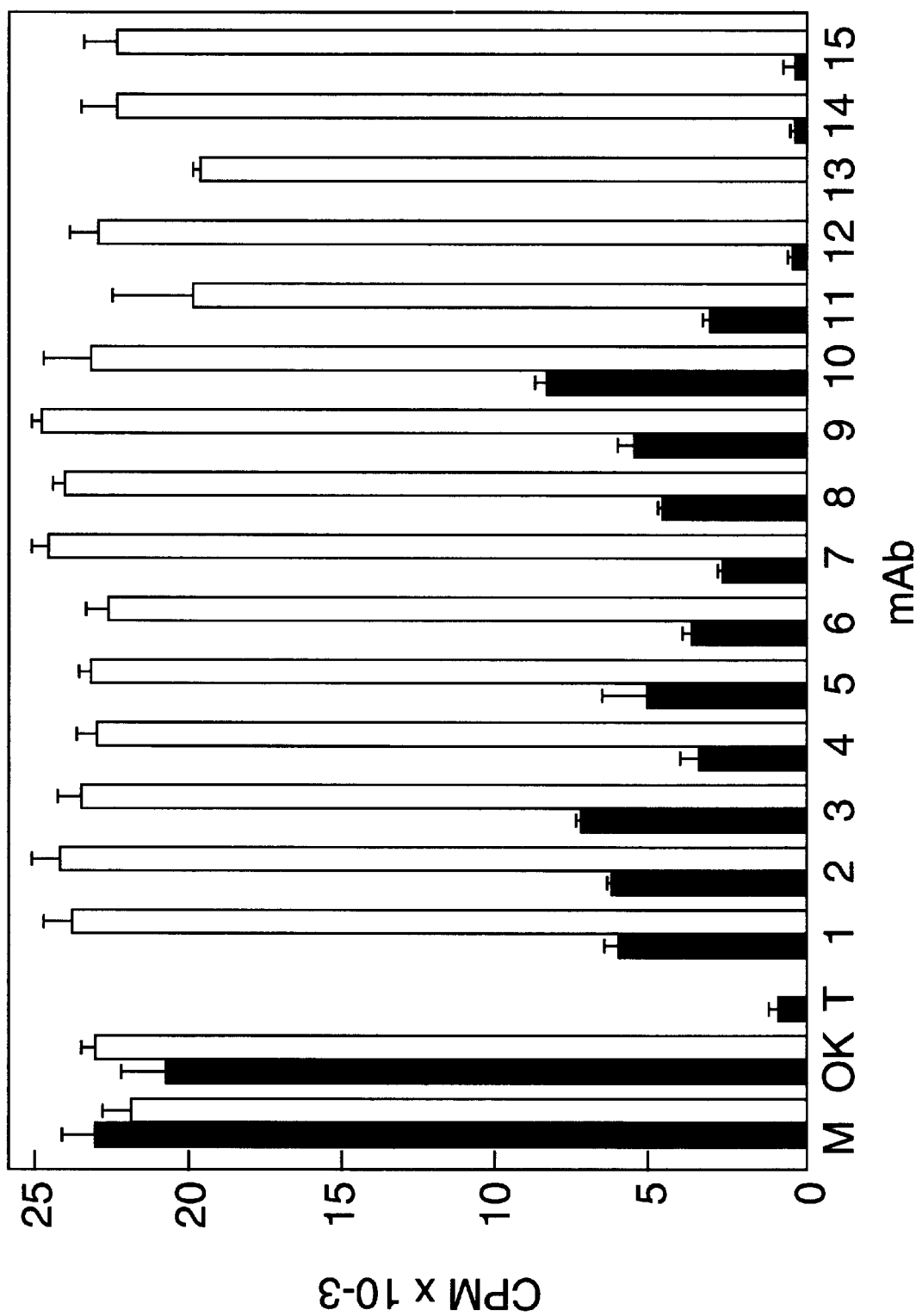
FIG. 1 shows a graph of the neutralization of IL-5 bioactivity in the BCL1 proliferation assay. Each mAb was incubated with either 1 μg/ml rhIL-5 (solid bar) or 1 ng/ml rmIL-5 (stippled bar). Each number indicates the respective anti-hIL-5 mAb, T=TRFK-5 (a positive control mAb for neutralization), OK=media (no mAb). Samples were assayed in triplicate and data are expressed as mean ±SE.

The potential role of IL-5 in the pathogenesis of inflammatory disorders suggests that the interaction of IL-5 with its receptor can be targeted by IL-5 derivatives, and by IL-5 mimetic agents in order to modulate this response. The present invention provides antibodies, and most preferably murine antibodies that are capable of specific binding to human IL-5 ("hIL-5"). As discussed below, such antibodies can be used in immunoassay formats to assay IL-5 expression. They also permit the identification of domains and/or residues of IL-5 that are functionally relevant to the biological activity of the molecule.

I. Interleukin-5

Interleukin-5 (IL-5) is a homodimeric cytokine secreted predominantly by activated Th2 lymphocytes (Clutterback, E., et al., *Eur. J. Immunol.* 17:1743 (1987); Takatsu, K., et al., *Immun. Rev.* 102:107 (1988); Enokihara, H., et al., *Blood* 73:1809 (1989), Parronchi, P., et al., *Eur. J. Immunol.* 22:1615 (1992); Schrezenmeier, et al., *Int. Soc. Exp. Hemat.* 21:358 (1993)). The homodimer is covalently linked by two disulfide bonds in a head-to-tail configuration (McKenzie, A. H. J., et al., *Molecular Immunology* 3:155 (1991); Tsuruoka N., et al., *Cell. Immun.* 125:354 (1990); Minamitake, Y., et al., *J. Biochem.* 107:292 (1990)). Dimer formation is absolutely essential for biological activity as monomeric IL-5 does not bind its receptor (McKenzie, A. H. J., et al., *Molecular Immunology* 3:155 (1991); Tsuruoka N., et al., *Cell. Immun.* 125:354 (1990); Takahashi T., et al., *Molecular Immunology* 27:911 (1990); Tominaga, A., et al., *J. Immunology* 144:1345 (1990)). IL-5 is heterogeneously gylcosylated with both N-and O-linked residues. Although these residues' may provide some thermal stability (Tominaga, A., et al., *J. Immunology* 144:1345 (1990)), they are not required for biological activity (Kodama, S., et al., *Eur. J. Biochim.* 211:903 (1993); Proudfoot, A. E. I., et al., *Biochem. J.* 270:357 (1990)). Murine IL-5 (mIL-5) and human IL-5 (hIL-5) share 73 percent amino acid homology (McKenzie, A. N. J., et al., *EMBO* 10:1193 (1991)), which enables cross-species reactivity in various bioassays. However, while human IL-5 ("hIL-5") and murine IL-5 ("mIL-5") act equally well in human cell assays, mIL-5 is greater than 100 fold more potent in murine cell assays (Plaetinch, G., et al., *J. Exp. Med.* 172:683 (1990)). This difference in potency provides an excellent system in which to study species specific IL-5 domains. Using murine/human chimeric constructs of IL-5, species specific activity has been localized to the C-terminal 36 amino acid residues (McKenzie, A. N. J., et al., *EMBO* 10:1193 (1991)).

Recently the crystal structure of hIL-5 was solved revealing two four-a-helix bundle motifs situated about a two fold axis of symmetry (Milburn, M. V., et al., *Nature* 363:172 (1993)). Although a four-a-helix bundle motif is characteristic for many cytokines, the IL-5 motif is unique in that for each bundle the three N-terminal helices of a given chain are complemented by the C-terminal helix from the other chain.

Murine IL-5 has been characterized for its effects on growth, differentiation and activation of both B-cells and eosinophils (Kyoshi, T., *Microbiol. Immunol.* 35:593 (1991)). It has also been demonstrated to induce differentiation of thymocytes to cytolytic T-cells and enhance their killing activity (Takatsu, K., et al., *Proc. Natl. Acad. Sci. (U.S.A.)* 84:4232 (1987); Aoki, T., et al., *J. Exp. Med.* 170:583 (1989)). Although the effect of hIL-5 on B-cells is controversial (Asuma, C., et al., *Nucleic Acid Research* 14:9146 (1986); Yokata, T., et al., *Proc. Natl. Acad. Sci. U.S.A.* 84:7388 (1987); Clutterbuck, E., et al., *Eur. J. Immu-* nol. 17:1743 (1987)). its effects on other hematopoietic cells is better established. Best characterized is the effects of hIL-5 on eosinophils. Human IL-5 selectively induces eosinophil differentiation and proliferation (Enokihara, H., et al., *Blood* 73:1808 (1989); Hirohisa, S., et al., *Proc. Natl. Acad. Sci. (U.S.A.)* 85:2288 (1988)), increases eosinophil survival (Yamagushi, Y., et al., *Blood* 78:2542 (1991); Wallen, N., et al., *J. Immunol.* 147:3490 (1991); Stern, M., et al., *J. Immunol.* 148:3543 (1992)), and acts as an iosinophil chemotactic factor (Coeffier, E., et al., *J. Immunol.* 147:2595 (1991); Wang, J. M., et al., *Eur. J. Immunol.* 19:701 (1989)). Eosinophil effector functions are enhanced by hIL-5 as well (Coeffier, E., et al., *J. Immunol.* 147:2595 (1991); Wang, J. M., et al., *Eur. J. Immunol.* 19:701 (1989); Fujisawa, T., et al., *J. Immunol.* 144:642 (1990)). IL-5 can enhance differentiation and activation of basophils, including the release of histamine and leukotrienes (Denburg, J. A., et al., *Blood* 77:2472 (1991); Hirai, K., et al., *J. Exp. Med.* 172:1525 (1990); Bischoff, S. C., et al., *J. Exp. Med.* 172:1577 (1990)). These many effects have implicated hIL-5 in the pathogenesis of asthma, allergy, and hypereosinophilic disorders (Robinson, D. S., et al., *N. Engl. J. Med.* 326:298 (1992); Hamid, Q., et al., *J. Clin. Invest.* 87:1541 (1991); Corrigan, C. J., et al., *Am Rev. Respir. Dis.* 147:540 (1993); Durham, S., et al., *J. Immunol.* 148:2390 (1992); Sehmi, R., et al. *Blood* 79:2952 (1992); Ohnishi, T., et al., *Am. Rev. Respir. Dis.* 147–901 (1993)).

II. The Production of Monoclonal Antibodies against Interleukin-5

Any of a variety of methods can be used to permit the production of monoclonal antibodies that are capable of specific binding to IL-5. In one embodiment, IL-5 can be purified from natural sources, in order to obtain samples sufficient to immunize an animal. Most preferably, the IL-5 immunogen will be produced via recombinant means through the cloning and expression of recombinant hIL-5 ("rhIL-5"). One aspect of the present invention concerns the capacity to produce high levels of substantially purified rhIL-5. As used herein, the term "substantially purified" rhIL-5 is intended to describe a rhIL-5 preparation which is substantially or completely lacks one or more portein, lipid, or carbohydrate that is normally associated with, or present in crude preparations of human IL-5.

A. The Cloning of Human IL-5 cDNA

Most preferably, such cloning is accomplished by adapting a hIL-5 cDNA sequence into a vector capable of expression in a baculoviral expression system (see, Summers, M. D., et a., *A Manual Of Methods For Baculovirus Vector And Insect Cell Culture Procedures*, The Texas Agricultural Experiment Station, College Station, Tex. (1987)). A preferred source of hIL-5 cDNA is plasmid phIL5 115.1, which is obtainable from the American Type Culture Collection, Rockville, Md., U.S.A. as accession number ATCC 59394. The original cDNA was isolated and cloned into pcDVI vector by Yokata, T., et al., *Proc. Natl. Acad. Sci. U.S.A.* 84:7388 (1987)) using a homopolymeric tailing method. This insert including G-C tails was excised from its original vector and inserted in to the BamH1 side of PBR 322 by the ATCC.

It is desirable to modify the ATCC 39394 vector in order to maximize expression. Specifically, high levels of expression can be obtained by modifying the plasmid such that the normal hIL-5 start codon becomes out of frame and downstream of the mutated polyhedron start codon, ATT. The modified vector is preferably co-transfected with wild type AcMNPV, or its equivalent, into a suitable cell line, such as the Sf9 cell line, and recombinant viruses picked and subcloned by plaque assay and hybridization using standard methodology (Summers, M.D., et al., *A Manual Of Methods For Baculovirus Vector And Insect Cell Culture Procedures*, The Texas Agricultural Experiment Station, College Station, Tex. (1987)).

Recombinant hIL-5 (rhIL-5) was preferably produced in spinner flasks of Sf9 cells using a multiplicity of infection of approximately ten. Preferably, the cell culture is filtered after several days of infection, and the supernatant is recovered, treated with detergents, and passed over a CnBr-Sepharose column that has been derivatized with the antibody to murine IL-5. The preferred murine antibody for this purpose is TRFK-5 (Mita, S., et al., *J. of Immunol. Meth.* 125:233 (1987)). Most preferably, the column purification of rhIL-5 is conducted as described by Schumacher, J. H., et al. (*J. Immuno.* 141–1576 ) (1988)). The purity of the recovered rhIL-5 can be tested by silver staining following SDS-PAGE and can be quantiated using the microliter BCA protein assay (Pierce, Rockford, Ill.) and by ELISA using TRFK-5 in a double antibody sandwich as described (Mita, S., et al., *J. of Immunol. Meth.* 125:233 (1987)). Functional quantitation can be done using the murine BCL, proliferation assay (Mita, S., et al., *J. Immunol. Meth.* 125:233 (1987)).

B. The Induction of Monoclonal Antibodies

Monoclonal antibodies that are capable of specific binding to hIL-5 are preferably produced by immunizing mice with the above-described affinity-purified rhIL-5.

BALB/c mice are preferred for this purpose, however, equivalent strains may also be used. The animals are preferably immunized with approximately 25 $\mu$g of affinity purified baculovirus derived rhIL-5 that has been emmusified 1:1 in TiterMax adjuvant (Vaxcel, Norcross, Ga.). Immunization is preferably conducted at two intramuscular sites, one intraperitoneal site, and one subcutaneous site at the base of the tail. An additional i.v. injection of approximately 25 $\mu$g rhIL-5 is preferably given in normal saline three weeks later. After approximately 11 days following the second injection, the mice may be bled and the blood screened for the presence of anti-hIL-5 antibodies. Preferably, a direct binding ELISA is employed for this purpose.

Most preferably, the mouse having the highest anti-hIL-5 titer is given a third i.v. injection of approximately 25 $\mu$g rhIL-5. The splenic leukocytes from this animal may be recovered 3 days later, and are then permitted to fuse, most preferably, using polyethylene glycol,. with cells of a suitable myeloma cell line. A preferred myeloma cell line is the p3X63Ag8.653 myeloma cell line. Hybridoma cells are selected by culturing the cells under "HAT" (hypoxanthine-aminopterin-Thymine) selection for about one week. The resulting clones may then be screened for their capacity to produce monoclonal antibodies ("mAbs") to hIL-5 ("anti-hIL-5"), preferably by direct ELISA.

High level production of the anti-hIL-5 mAbs was obtained using nude mice. Nude mice are primed with 0.5 ml of 2,6,10,14-tetramethypentadecane (Aldrich, Milwaukee, Wis.). After approximately 5 days, each clone is harvested, pelleted, and resuspended in sterile PBS to a final destiny of approximately $2.5 \times 10^6$ cell/ml. A pair of nude mice were injected for each monoclonal antibody. Antibody may be recovered from the ascites fluid of the animals, and is preferably lipocleaned with Seroclear (Calbiochem, San Diego, Calif.) following vender specifications. The mAbs may then be further purified, preferably using a GamaBind Plus Sepharose column (Pharmacia, Uppsala, Sweden). Eluted MAb is preferably concentrated and dialyzed against saline. The concentration of the antibody may be determined using absorbance of light at 280 nm. Monoclonal antibodies can be isotyped using the Mouse MonAB ID KIT (HRP) (Zymed, San Francisco, Calif.). Biotinylated MAB (b-mAb) were generated for each clone as described by (Harriman, G. G., In: *Current Protocols in Immunology*, vol. 1., Coligan, J. E. et al., eds., Greene Publishing Associates and Wiley-Interscience, New York, N.Y., p. 6.5.1 (1991)) for use in ELISA.

III. The Molecules of the Present Invention

The present invention concerns recombinantly produced human IL-5, as well as mutants and mimetics of IL-5. The invention also concerns antibodies, and binding molecules that are capable of specific binding to IL-5. The characteristics of these molecules are discussed below.

A. Antibodies and Binding Molecules Capable of Specifically Binding with hIL-5

The present invention concerns the production and use of molecules that are capable of "specific binding" to one another. As used herein, a molecule is said to be capable of "specific binding" to another molecule, if such binding is dependent upon the respective structures of the molecules. The known capacity of an antibody to bind to an immunogen is an example of "specific binding." Such interactions are in contrast to non-specific binding that involve classes of compound, irrespective of their chemical structure (such as the binding of proteins to nitrocelulose, etc.) Most preferably, the antibody and other binding molecules of the present invention will exhibit "highly specific binding," such that they will be incapable of substantially incapable of binding to closely related heterologous molecules. Indeed, the preferred monoclonal antibodies of the present invention exhibit the capacity to bind to human IL-5, but are substantially incapable of binding murine IL-5; such antibodies are capable of highly specific binding to human IL-5, as those terms are used herein.

The above-described divalent antibody molecules (i.e. possessing two IL-5 binding domains) comprise one class of the immunoglobulin reagents of the present invention, however, the invention also includes derivatives and modified immunoglobulins that have the capacity to specifically bind to human IL-5.

Thus, in one embodiment, such molecules will comprise fragments (such as (F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecules (such as two different IL-5 epitopes), or they may be capable of binding to an IL-5 epitope and a "non-IL-5" epitope. In one embodiment, such "non-IL-5" epitopes are selected such that the chimeric molecule can bind to cellular receptors, such as hormone receptors, immune response receptors, etc. Because such a molecule can bind to IL-5, it may be used to "ferry" IL-5 to any cell that arrays such cellular receptors, regardless of whether the cell expresses the IL-5 receptor.

In one embodiment, any of the above-described molecules can be labelled, either detectably, as with a radioisotope, a paramagnetic atom, a fluorescent moiety, an enzyme, etc. in order to facilitate the its detection in, for example, in situ or in vivo assays. In an alternative embodiment, the molecules can be labelled with a toxin molecule in order to provide a cell receptor specific targeting of the toxin. The molecules may be labelled with reagents such as biotin, in order to, for example, facilitate their recovery, and/or detection.

The monoclonal antibodies of the present invention have been found to comprise two antigenic groups, and to thereby establish that human IL-5 contains multiple epitopes that can be recognized by murine splenocytes. The specificity of these antibodies to hIL-5 was assessed by direct ELISA. All mAb bound only rhIL-5. No binding was detected with baculovirus-expressed murine IL-5 indicating that the observed anti-hIL-5 mAb binding was not specific to Sf9 cell glycosylation of the rhIL-5.

By competitive ELISA, all mAb could be divided between two binding groups, A and B. Group A consisted of eleven mAb and group B consisted of four mAb which competed for TRFK-5 binding to hIL-5. No further distinction could be made within a given group, as competition could be a result of epitope identify or merely steric interference between a given pair of mAb within each group. However since TRFK-5 is capable of binding mIL-5, its epitope cannot be the same as any recognized by any group B mAb. Thus competition for binding between TRFK-5 and group B mAb must be a result of steric hinderance. Therefore, at least three epitopes have been demonstrated for hIL-5, all of which are neutralizing. Through ELISA and Western analysis these mAb have been further characterized and subdivided, and found to define two epitopes of human IL-5. The isolation of the antibodies permits the design of fragments and derivatives.

Where the antibodies or their fragments are intended for therapeutic purposes, it may desirable to "humanize" them in order to attenuate any immune reaction. Humanized antibodies may be produced, for example by replacing an immunogenic portion of an antibody with a corresponding, but non-immunogenic portion (i.e. chimeric antibodies) (Robinson, R. R. et al., International Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., *Science* 240:1041–1043 (1988); Liu, A. Y. et al., *Proc. Natl. Acad. Sci. USA* 84:3439–3443 (1987); Liu, A. Y. et al., *J. Immunol.* 139:3521–3526 (1987); Sun, L. K. et al., *Proc. Natl. Acad. Sci. USA* 84:214–218 (1987); Nishimura, Y. et al., *Canc. Res.* 47:999–1005 (1987); Wood, C. R. et al., *Nature* 314:446–449 (1985)); Shaw et al., *J. Natl. Cancer Inst.* 80:1553–1559 (1988); all of which references are incorporated herein by reference). General reviews of "humanized" chimeric antibodies are provided by Morrison, S. L. (*Science*, 229:1202–1207 (1985)) and by Oi, V. T. et al., *Bio Techniques* 4:214 (1986); which references are incorporated herein by reference).

Suitable "humanized" antibodies can alternatively be produced by CDR or CEA substitution (Jones, P. T. et al., *Nature* 321:552–525 (1986); Verhoeyan et al., *Science* 239:1534 (1988); Beidler, C. B. et al., *J. Immunol.* 141:4053–4060 (1988); all of which references are incorporated herein by reference).

B. hIL-5 Mutants and Mimetic Agents

The identification of the monoclonal antibodies of the present invention permits the design and development of hIL-5 mutants and mimetic agents. Such agents can be used to treat inflammatory diseases such asthma; adult respiratory distress syndrome (ARDS) or multiple organ injury syndromes secondary to septicemia or trauma; reperfusion injury of myocardial or other tissues; acute glomerulonephritis; reactive arthritis; dermatoses with acute inflammatory components; eosinophilia; acute purulent meningitis or other central nervous system inflammatory disorders; thermal injury; hemodialysis; leukapheresis; ulcerative colitis; Crohn's disease; necrotizing enterocolitis; granulocyte transfusion associated syndromes; cytokine-induced toxicity, as well as aberrant responses of the specific defense system include the response to antigens such as rubella virus, autoimmune diseases, delayed type hypersensitivity response mediated by T-cells.

In particular, the epitopes of hIL-5 recognized by the antibodies of the present invention define sites of probable importance to the structure or functions of IL-5. Since the cDNA sequence that encodes hIL-5 is known, it is possible to mutate or alter that sequence via classical or recombinant means. Such mutated gene sequences can be expressed and evaluated for their capacity to bind the antibodies of the present invention. In this manner, mutant IL-5 species can be isolated and evaluated for their capacity to inhibit IL-5-mediated inflammation, or other IL-5 functions. Similarly, such species can be evaluated for their capacity to induce a hyper inflammatory response, such as would be desirable in immune compromised or immune suppressed individuals (for examples, AIDS or ARC patients).

In one embodiment, such molecules are derived via mutagenesis of IL-5, or from polypeptide fragments of the IL-5 molecule. Such fragments can be prepared via chemical or recombinant means (such as by randomly cleaving IL-5-encoding DNA and then incorporating the cleavage fragments into translatable expression vectors). In this manner, a library of different peptide fragments can be obtained and evaluated. The biological activity of the polypeptides can be assessed by the immunoassays described herein, or by the capacity of the molecules to bind to anti-IL-5 antibody columns.

IL-5 mutant analogs can be identified either rationally, as described below, or via established methods of mutagenesis (see, for example, Watson, J. D. et al., *Molecular Biology of the Gene*, Fourth Edition, Benjamin/Cummings, Menlo Park, Calif. (1987). Significantly, a random mutagenesis approach requires no *a priori* information about the gene sequence that is to be mutated. This approach has the advantage that it assesses the desirability of a particular mutant on the basis of its function, and thus does not require an understanding of how or why the resultant mutant protein has adopted a particular conformation. Indeed, the random mutation of target gene sequences has been one approach used to obtain mutant proteins having desired characteristics (Leatherbarrow, R. J. *Prot. Eng.* 1:7–16 (1986); Knowles, J. R., *Science* 236:1252–1258 (1987); Shaw, W. V., *Biochem. J.* 246:1–17 (1987); Gerit, J. A. *Chem. Rev.* 87:1079–1105 (1987)). Alternatively, where a particular sequence alteration is desired, methods of site-directed mutagenesis can be employed. Thus, such methods may be used to selectively alter only those amino acids of the protein that are believed to be important (Craik, C. S., *Science* 228:291–297 (1985); Cronin, C. S. et al., *Biochem.* 27:4572–4579 (1988); Wilks, H. M. et al., *Science* 242:1541–1544 (1988)). The analysis of such mutants can also be facilitated through the use of a phage display protein ligand screening system (Lowman, H. B. et al., *Biochem.* 30:10832–10838 (1991); Markland, W. et al., *Gene* 109:13–19 (1991); Roberts, B. L. et al., *Proc. Natl. Acad. Sci.* (*U.S.A.*) 89:2429–2433 (1992); Smith, G. P., *Science* 228:1315–1317 (1985); Smith, R. P. et al., *Science* 248:1126–1128 (1990), all herein incorporated by reference)). In general, this method involves expressing a fusion protein in which the desired protein ligand is fused to the C-terminus of a viral coat protein (such as the M13 Gene III coat protein, or a lambda coat protein).

The antibodies of the present invention can alternatively be used to screen molecules other than IL-5 (or IL-5 fragments) for their capacity to mimic one or more functions of IL-5. Such functions include not only the biological activities of the molecule, but also the capacity of IL-5 to bind to its normal cellular receptor molecule. Indeed, mimetic agents that are capable of binding to the IL-5 receptor, but are substantially incapable of mediating other IL-5 functions are highly desired. The present invention provides a means for obtaining such molecules.

Thus, the present invention concerns mimetic analogs of IL-5. As used herein, a "mimetic analog" of hIL-5 is a molecule that retains a biological activity of the molecule, but will typically be unrelated chemically. An organic molecule whose structure mimics the active site, or a binding site of hIL-5 would comprise a "mimetic analog" of that protein. The hIL-5 mimetic agents of the present invention may be an oligonucleotides, a proteinaceous compound (including both glycosylated and non-glycosylated proteins), or a non-proteinaceous compound (such as a steroid, a glycolipid, etc.) provided that the agent mimics a function of either an entire hIL-5 nucleic acid molecule, or a fragment thereof. Preferred classical analogs include polypeptides (including circular as well as linear peptides) whose sequences comprise the active catalytic or binding sites of an hIL-5 protein, or oligonucleotide fragments of nucleic acid hIL-5 molecules that are capable of either repressing or inducing hIL-5 activity. Preferred mimetic analogs include polypeptides that are not fragments of an hIL-5 protein, or mutants thereof, but nevertheless exhibit a capacity to induce senescence in an hIL-5-like manner, or to induce cellular proliferation in the manner of an hIL-5 antagonist.

Mimetic analogs of naturally occurring hIL-5 molecules may be obtained using the principles of conventional or of rational drug design (Andrews, P. R. et al., In: *Proceedings of the Alfred Benzon Symposium*, volume 28, pp. 145–165, Munksgaard, Copenhagen (1990); McPherson, A. *Eur. J. Biochem.* 189:1–24 (1990); Hol, W. G. J. et al., In: *Molecular Recognition: Chemical and Biochemical Problems*, Roberts, S. M. (ed.); Royal Society of Chemistry; pp. 84–93 (1989); Hol, W. G. J., *Arzneim-Forsch.* 39:1016–1018 (1989); Hol, W. G. J., *Agnew, Chem. Int. Ed. Engl.* 25:767–778 (1986) all herein incorporated by reference).

In accordance with the methods of conventional drug design, the desired mimetic molecules are obtained by randomly testing molecules whose structures have an attribute in common with the structure of a "native" hIL-5 molecule, or a molecule that interacts with an hIL-5 molecule. The quantitative contribution that results from a change in a particular group of a binding molecule can be determined by measuring the capacity of competition or cooperatively between the native hIL-5 molecule and the putative mimetic.

In one embodiment of rational drug design, the mimetic is designed to share an attribute of the most stable three-dimensional conformation of an hIL-5 molecule. Thus, the mimetic analog of a hIL-5 molecule may be designed to possess chemical groups that are oriented in a way sufficient to cause ionic, hydrophobic, or van der Waals interactions that are similar to those exhibited by the hIL-5 molecule. In a second method of rational design, the capacity of a particular hIL-5 molecule to undergo conformational "breathing" is exploited. Such "breathing"—the transient and reversible assumption of a different molecular conformation—is a well appreciated phenomenon, and results from temperature, thermodynamic factors, and from the catalytic activity of the molecule. Knowledge of the 3-dimensional structure of the hIL-5 molecule (Milburn, M. W. et al., *Nature* 363:172–176 (1993); herein incorporated by reference) facilitates such an evaluation. An evaluation of the natural conformational changes of an hIL-5 molecule facilitates the recognition of potential hinge sites, potential sites at which hydrogen bonding, ionic bonds or van der Waals bonds might form or might be eliminated due to the breathing of the molecule, etc. Such recognition permits the identification of the additional conformations that the hIL-5 molecule could assume, and enables the rational design and production of mimetic analogs that share such conformations.

The preferred method for performing rational mimetic design employs a computer system capable of forming a representation of the three-dimensional structure of the hIL-5 molecule (such as those obtained using RIBBON (Priestle, J., *J. Mol. Graphics* 21:572 (1988)), QUANTA (Polygen), InSite (Biosyn), or Nanovision (American Chemical Society). Such analyses are exemplified by Hol, W. G. J. et al. (In: *Molecular Recognition: Chemical and Biochemical Problems*, Roberts S. M. (ed.); Royal Society of Chemistry; pp. 84–93 (1989), Hol, W. G. J. (*Arzneim-Forsch.* 39:1016–1018 (1989)), and Hol, W. G. J., *Agnew. Chem. Int. Ed. Engl.* 25:767–778 (1986)).

IV. The Uses of the Molecules of the Present Invention

The anti-hIL-5 antibodies of the present invention can be used to isolate, characterize, and quantitate hIL-5. They may also be used to effect the precise mapping of those hIL-5 epitopes critical for binding to the IL-5 receptor (Limaye, A. P., et al., *J. Clin. INvest.* 88:1418 (1991)). Moreover, since anti-mIL-5 monoclonal antibodies can block mIL-5 mediated eosinophilia in both mice and guinea pigs (Bloom, J. W., et al., *J. Immunol.* 151:2707 (1993); Coffman, R. L., et al., *Science* 245:308 (1989); Rennick, D. M., et al., *Blood* 76:312 (1990); Owen, W. F., et al., *J. Exp. Med.* 170:343 (1989); Chand, N., et al., *Eur. J. Pharm* 211:121 (1991)), the anti hIL-5 mAb of the present invention has utility in blocking IL-5 mediated inflammation in humans.

A. Immunoassay Analysis of hIL-5 Expression

The present invention provides a highly sensitive immunoassay suitable for detecting and/or quantitating the presence of human interleukin-5 in a sample. As used herein, the term "sample" is intended to encompass biological specimens derived from a human or other animal source (such as, for example, blood, stool, sputum, mucus, serum, urine, saliva, teardrop, a biopsy sample, an histology tissue sample, a PAP smear, etc.) including samples derivated a cellular preparation (such as a cellular extract, lysate, cytosol, etc.). As will be understood, the sample may need to be diluted with buffer, or concentrated (as with an evaporator or lyophilizer) in order to ensure that the amount of IL-5 contained in the sample is within the detection limits of the assay.

As will be understood from the well-known principles of immunoassays, alternative formats, such as immunometric assays (also known as a "two-site" or "sandwich" assays), including both "forward," "simultaneous" and "reverse" assays. For example, in a "forward" assays, antibody would be bound to a solid support (such as a microtiter plate, test tube, dipstick, etc.), and then first contacted with the sample being tested to extract the hIL-5 from the sample by formation of a binary solid phase antibody-hIL-5 complex. After incubation and washing, the support would be placed in contact with a quantity of labeled antibody specific for hIL-5 (which functions as a "reporter"). After a second incubation period to permit the labeled antibody to complex with the hIL-5 bound to the solid support through the unlabeled antibody, the solid support would be washed a second time to remove the unreacted labeled antibody. This type of forward sandwich assay may be a simple "yes/no" assay to determine whether hIL-5 is present or may be made quantitative by comparing the amount of retained labeled antibody with that obtained for a standard sample containing known quantities of hIL-5. Such "two-site" or "sandwich" assays are described by Wide, In: *Radioimmune Assay Method,* (Kirkham et al., Ed.), E. & S. Livingstone, Edinburgh, pp 199–206 (1970), herein incorporated by reference).

In a "simultaneous" assay, a single incubation step is employed in which the bound antibody and the labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In a "reverse" assay, a solution of labeled antibody is incubated with the fluid sample followed. After such incubation, the mixture is placed in contact with a solid support to which unlabeled antigen has been previously bound. After a second incubation, the solid phase is washed in a conventional fashion to free it from the residue of the sample being tested and the solution of unreacted labeled antibody. The determination of labeled antibody associated with a solid support is then determined as in the "simultaneous" and "forward" assays.

In its most preferred embodiment, the ELISA of the present invention employs an anti-hIL-5 monoclonal antibody. Most preferably, such antibodies are generated by immunizing a heterologous mammal (such as a mouse, rat, rabbit, etc.) with hIL-5, and then harvesting the splenic leukocytes of the animal, and fusing them with a suitable myeloma cell, in the manner described above. In one embodiment, such monoclonal antibodies can be directly employed in an immuoassay format. Alternatively, such antibodies may be cleaved or processed to form fragments that retain the capacity to bind hIL-5. Examples of such fragments include (F(ab'), F(ab')$_2$ fragments. The fragments can be directly used to assay IL-5 expression, or they can be combined with fragments of other antibodies in order to form non-naturally occurring "divalent" or "multivalent" antibodies. Such antibodies could, for example, therefore possess the capacity to bind to multiple epitopes of IL-5, or to an epitope of IL-5 and an epitope of another molecule.

Suitable solid supports may be composed, for example, of materials such as glass, paper, polystyrene, polypropylene, polyethylene, dextran, nylon, amylases, natural and modified celluloses, polyacrylamides, agaroses, or magnetite. The nature of the support can be either soluble to some extent or insoluble for the purposes of the present invention. The support material may have virtually any possible structural configuration so long as the bound IL-5 is capable of binding to an anti-IL-5 antibody. Thus, the support configuration may be spherical, as in a bead, or cylindrical, as in the inside surface of a test tube, or the external surface of a rod. Alternatively, the surface may be flat such as a sheet, test strip, etc. Those skilled in the art will note many other suitable carriers for binding monoclonal antibody, or will be able to ascertain the same by use of routine experimentation. Most preferably, the support will be a polystyrene microtiter plate.

B. Antibody-Enhanced Purification or Recovery of IL-5

The antibodies of the present invention can be employed to enable a rapid recovery of substantially pure IL-5 from either recombinant or natural sources (e.g. serum). Thus, such molecules can be used in large scale affinity chromatography to effect the removal of IL-5 from a supernatant. Significantly, since the antibodies of the present invention do not recognize murine IL-5, they are particularly suitable for use in purifying human IL-5 from sources that may be contaminated with the murine IL-5 homolog.

Thus, the antibodies of the present invention can be bound to a resin, such as sepharose. The treated resin can be incubated, either in batch, as a slurry, or, more preferably, as a continuous throughput column in order to effect such recovery.

C. IL-5 Mimetic Therapy

As indicated, one aspect of the present invention concerns therapeutic molecules that are capable of modulating the eosinophilic response induced by IL-5, and thus of attenuating an undesired inflammatory response. Conversely, The antibodies of the present invention can be used to obtain hyperinflammatory analogs of IL-5 that can be used in immune suppressed individuals.

Such therapeutic molecules of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A., Ed., Mack. Easton, Pa. (1980)). In order to form a pharmaceutically acceptable composition suitable for effective administration, such compositions will contain an effective amount of an antisense oligonucleotide, or its equivalent, or their functional derivatives, together with a suitable amount of carrier vehicle.

Additional pharmaceutical methods may be employed to control the duration of action. Control release preparations may be achieved through the use of polymers to complex or absorb an antisense oligonucleotide, or its equivalent, or their functional derivatives. The controlled delivery may be exercised by selecting appropriate macromolecules (for example polyesters, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate an antisense oligonucleotide, or its equivalent, or their functional derivatives, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcelluose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

The therapeutic compositions of the present invention can also be formulated for administration parenterally by injection, rapid infusion, nasopharyngeal absorption (intranasopharangeally), dermabsorption, or orally. The compositions may alternatively be administered intramuscularly, or intravenously. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers, adjucts or occlusive dressings can be used to increase tissue permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include wetting agents, emulsifying and suspending agents, or sweetening, flavoring, coloring or perfuming agents.

A therapeutic composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

Generally, the dosage needed to provide an effective amount of the composition will vary depending upon such factors as the recipient's age, condition, sex, and extent of disease, if any, and other variables which can be adjusted by one of ordinary skill in the art.

Having now generally described the invention, the same will be more readily understood through reference to the following examples which are provided by way of illustration, and are not intended to be limiting of the present invention, unless specified. In the Examples that follow, unless otherwise stated, all values represent mean of triplicate samples ±standard error of the mean. The Tukey test was used to compare groups. Significance was assigned by a P value of less than 0.05.

EXAMPLE 1

HIL-5 CLONING AND EXPRESSION

A hIL-5 cDNA containing plasmid [ph IL5 115.1] was obtained from the ATCC [#59394]. The original cDNA was isolated and cloned into pcDVI vector by Yokata, T., et al. (*Proc. Natl. Acad. Sci. U.S.A.*, 84:7388 (1987)) using a homopolymeric tailing method. This insert including G-C tails was excised from its original vector and inserted in to the BamH1 site of PBR 322 by the ATCC. To maximize efficiency of expression, we used PCR to insert a new BamHI site 30 bases upstream from the IL-5 start codon and recloned the insert into the BamHI site of baculovirus transfer vector, PVL 941. The PCR priming sequence [SEQ ID NO: 1 GAGGATCCAAAGGCAAACGCAGA] was chosen to place the hIL-5 start codon out of frame and 70 bases downstream of the mutated polyhedron start codon, ATT. The insert was sequenced in PVL 941 to insure sequence fidelity. The recombinant transfer vector, PVL-hIL-5, was cotransfected with wild type AcMNPV into the Sf9 cell line and recombinant viruses picked and subcloned by plaque assay and hybridization using standard methodology (Summers, M. D., et al., A manual of methods for baculovirus vector and insect cell culture procedures. The Texas Agricultural Experiment Station, College Station, Tex. (1987)). Recombinant hIL-5 (rhIL-5) was produced in 400 ml spinner flasks of Sf9 cells using an MOI of ten. After five days of infection, the cell culture supernate was filtered and made to 0.5% NP-40 and 0.05% tween 20 and run over a CnBr-Sepharose column derivatized with the anti-mIL-5 mAB, TRFK-5 (Mita, S., et al., *J. of Immunol. Meth.* 125:233 (1987)). The column was run essentially according to the method of Schumacher, J. H., et al., (*J. Immuno.* 141–1576 (1988)). Purified rhIL-5 was tested for purity by silver staining following SDS-PAGE and was quantiated using the microliter BCA protein assay (Pierce, Rockford, Ill.) and by ELISA using TRFK-5 in a double antibody sandwich as described (Mita, S., et al., *J. of Immunol. Meth.* 125:233 (1987))). Functional quantitation was done using the murine BCL, proliferation assay (Mita, S., et al., *J. Immunol. Meth.* 125:233 (1987)).

EXAMPLE 2

MONOCLONAL ANTIBODY GENERATION

BALB/c mice were immunized with 25 μg of affinity purified baculovirus derived rhIL-5 emulsified 1:1 in Titer-Max adjuvant (Vaxcel, Norcross, Ga.) at two intramuscular sites, one intraperitoneal site, and one subcutaneous site at the base of the tail. An additional i.v. injection of 25 μg rhIL-5 was given in normal saline three weeks later. Mice were bled 11 days following the second injection and screened from anti-hIL-5 antibodies in a direct binding ELISA. The mouse with the highest anti-hIL-5 titer was given a third i.v. injection of 25 μg rhIL-5. Three days later splenic leukocytes were harvested and fused with P3X63Ag8.653 myeloma cells, using polyethylene glycol. After fusion, cells were plated on five 96 wells plates in 100 μl/well HAT selection media and incubated at 37° C. in 5% $CO_2$ air. After one week, all wells were screen for anti-hIL-5 activity again by direct binding ELISA and a select number of positive wells subcloned by three rounds of limiting dilutions. Fifteen clones were expanded stepwise to a T75 flask (Corning, Corning, N.Y.). Nude mice were primed with 0.5 ml of 2,6,10,14-tetramethypentadecane (Aldrich, Milwaukee, Wis.). After 5 days, each clone was harvested, pelleted, and resuspended in sterile PBS to a final density of $2.5 \times 10^6$ cell/ml. For all fifteen clones a pair of nude mice were injected i.p. using a 22-G needle with $5.0 \times 10^6$ cell. Ascites was collected daily by drainage using a 18-G needle and pooled for batch processing. Ascites was spun at 1000×g and the supernatant collected and lipocleaned with Seroclear (Calbiochem, San Diego, Calif.) following vendor specifications. Murine antibody was purified using a GammaBind Plus Sepharose column (Pharmacia, Uppsala, Sweden). Eluted MAb was concentrated and dialyzed against 0.15M NaCl. Concentration was determine using absorbance of light at 280 nm. Monoclonal antibodies were isotyped using the Mouse MonoAB ID Kit (HRP) (Zymed, San Francisco, Calif.). Biotinylated MAB (b-mAb) were generated for each clone as previously described (Harriman, G. R., In: *Current Protocols in Immunology*, vol. 1., Coligan, J. E. et al., eds., Greene Publishing Associates and Wiley-Interscience, New York, N.Y., p. 6.5.1 (1991)) for use in ELISA.

To assay for the production of anti-hIL-5 antibodies, polystyrene ELISA plates (Corning, Corning, N.Y.) were coated with either 50 μl of rhIL-5 or rmIL-5 (Harriman, G. R., In: *Current Protocols in Immunology*, vol. 1., Coligan, J. E. et al., eds., Greene Publishing Associates and Wiley-Interscience, New York, N.Y., p. 6.5.1 (1991)) at a concentration of 2 μg/ml in PBS and incubated overnight at 4° C. Plates were blocked with PBS 0.5% tween 10% calf serum. Fifty microliters of each biotinylated-mAb (b-mAb) at a 1/250 dilution in blocker plus a control without mAb were incubated. Fifty microliters of strepavidin-alkaline phosphatase (Molecular Probes, Inc., Eugene, Oreg.) at 1/500 dilution in blocker was incubated. Finally 100 μl of a 4-methylumbelliferylphosphate (MUP) (Sigma, St. Louis, Mo.) substrate solution (0.05 mg MUP/ml in 1 M diethanolamine 1 mM $MgCl_2$ pH 9.8) was added and placed on a shaker for 30 minutes at room temperature. Fluorescence was read on a Titertek Fluoroskan II fluorometer (Flow Laboratories, McLean, Va.) at 30 and 45 minutes). Fluorometric values were recorded using Titersoft II E.I.A. Software (Flow Laboratories, McLean Va.). Unless otherwise stated all incubations were done on a shaker at room temperature for one hour. Between each incubation step plates were washed five times with PBS 0.5% tween.

Following three rounds of limiting-dilution-cloning, fifteen hybridomas producing anti-rhIL-5 mAb were selected and given the designation IL5.1 through IL5.15. The hybridomas designated as IL5.1 through IL5.15 were deposited with the American Type Culture Collection (ATCC), 10801 University Boulevard, Manassas, Va. 20110-2209, on Jan. 13, 1999. IL5.1 was assigned the ATCC designation number HB-12637, and is referenced by the depositor as Murine hybridoma 5.1.1; IL5.2 was assigned ATCC number HB-12627, and is referenced as Murine hybridoma h5.1.2; IL5.3 was assigned ATCC number HB-12640, and is referenced as Murine hybridoma h5.1.3; IL5.4 was assigned ATCC number HB-12626, and is referenced as Murine hybridoma h5.2.1; IL5.5 was assigned ATCC number HB-12634, and is referenced as Murine hybridoma h5.2.2; IL5.6 was assigned ATCC number HB-12636, and is referenced as Murine hybridoma h5.2.3; IL5.7 was assigned ATCC number HB-12638, and is referenced as Murine hybridoma 5.2.4; IL5.8 was assigned ATCC number HB-12633, and is referenced as Murine hybridoma h5.3.1; IL5.9 was assigned ATCC number HB-12628, and is referenced as Murine hybridoma h5.3.2; IL5.10 was assigned ATCC number HB-12630, and is referenced as Murine hybridoma h5.4; IL5.11 was assigned ATCC number HB-12635, and is referenced as Murine hybridoma h5.5; IL5.12 was assigned ATCC number HB-12639, and is referenced as Murine hybridoma h5.6; IL5.13 was assigned ATCC number HB-12631, and is referenced as Murine hybridoma h5.7.1; IL5.14 was assigned ATCC number HB-12629, and is referenced as Murine hybridoma h5.7.2; and, IL5.15 was assigned ATCC number HB-12632, and is referenced as Murine hybridoma h5.7.3. All were of the isotype $IgG_1$, kappa. Each mAb was isolated from ascites fluid over protein G columns for determination of binding characteristics.

Using the previously characterized rat mAb, TRFK-5 (43), as a positive control, each murine mAb was screened by direct ELISA for binding to rhIL-5 and rmIL-5 (Table I). All anti-hIL-5 mAb bound selectively to rhIL-5 and lacked any binding to rmIL-5. In Table I, values are mean fluorescence units ±1; TRFK-5 is a positive control mAb for binding to both hIL-5 and mIL-5.

TABLE I

Binding of mAb to IL-5 By Direct ELISA

| mAb | rhIL-5 | rmIL-5 |
|---|---|---|
| IL5.1 | 6292 ± 110 | 0 ± 5 |
| IL5.2 | 6012 ± 58 | 0 ± 5 |
| IL5.3 | 6028 ± 115 | 0 ± 14 |
| IL5.4 | 6020 ± 119 | 0 ± 6 |
| IL5.5 | 6096 ± 113 | 0 ± 6 |
| IL5.6 | 6106 ± 137 | 0 ± 4 |
| IL5.7 | 6138 ± 110 | 0 ± 5 |
| IL5.8 | 6374 ± 85 | 0 ± 5 |
| IL5.9 | 6217 ± 62 | 0 ± 3 |
| IL5.10 | 5879 ± 35 | 0 ± 5 |
| IL5.11 | 5895 ± 20 | 0 ± 4 |
| IL5.12 | 6015 ± 14 | 0 ± 31 |
| IL5.13 | 5955 ± 8 | 0 ± 5 |
| IL5.14 | 5883 ± 36 | 0 ± 6 |
| IL5.15 | 5812 ± 2 | 0 ± 3 |
| TRFK-5 | 6392 ± 122 | 5916 ± 1 |
| no MAb | 0 ± 1 | 0 ± 1 |

Thus, a panel of fifteen mAb were generated against baculovirus expressed rhIL-5. All mAb were of the isotype IgG$^1$, Kappa. All were specific for hIL-5 and capable of neutralizing hIL-5 biological activity. Through ELISA and Western analysis these mAb have been further characterized and subdivided. Although they have already been proven useful for isolating, characterizing, and quantitating hIL-5, they should facilitate precise mapping of hIL-5 epitopes critical for binding to the IL-5 receptor (Limaye, A. P., et al., *J. Clin. INvest.* 88:1418 (1991)). The ability of mAb to block

EXAMPLE 3

COMPETITIVE BINDING ELISA

Differences in rhIL-5 binding among the mAb were assessed by competitive ELISA. Binding of each b-mAb was completed with a 100-fold excess of each unlabeled mAb.

Polystyrene ELISA plates (Corning, Corning, N.Y.) were coated with 50 μl of rhIL-5 (2 μg/ml in PBS) and incubated overnight at 4° C. Plates were blocked with PBS 0.5% tween 10% calf serum. To assess competitive binding, 50 μl in blocker) of each unlabeled mAb was preincubated in a block of wells. Buffer without mAb was added to a block of control wells. Without washing, fifty microliters of each b-mAb (0.25 μg/ml in blocker) were then added to a pair of wells in each block and incubated for another hour at room temperature. The same strepavidin-alkaline phosphatase/MUP detection system described above was used to determine the degree of b-mAb binding.

As shown in Table II, all mAb could be divided into one of two ELISA binding groups. Group A consisted of mAb IL5.1 through IL5.11. Group B consisted of IL5.12 through IL5.15. TRFK-5 was also found to compete for binding with all group B anti-hIL-5 mAb and was thus assigned to that binding group. Results were represented as percent inhibition of maximum binding, defined as the signal generated by each b-mAb in the absence of any competing mAb. A given b-mAb competing with itself represented the maximum inhibition achievable.

TABLE II

Analysis of anti-hIL-5 mAb binding by competitive ELISA[a]

| Biotinylated mAb | Competing mAb Group A | | | | | | | | | | | Group B | | | | |
|---|---|---|---|---|---|---|---|---|---|---|---|---|---|---|---|---|
| | IL5.1 | IL5.2 | IL5.3 | IL5.4 | IL5.5 | IL5.6 | IL5.7 | IL5.8 | IL5.9 | IL5.10 | IL5.11 | IL5.12 | IL5.13 | IL5.14 | IL5.15 | TRFK-5 |
| b-IL5.1 | 94 | 94 | 93 | 96 | 97 | 96 | 97 | 95 | 94 | 94 | 97 | 0 | 0 | 0 | 0 | 0 |
| b-IL5.2 | 95 | 96 | 95 | 97 | 98 | 98 | 98 | 96 | 94 | 96 | 97 | 0 | 0 | 0 | 0 | 0 |
| b-IL5.3 | 95 | 95 | 94 | 95 | 98 | 98 | 98 | 95 | 93 | 95 | 96 | 0 | 0 | 0 | 0 | 0 |
| b-IL5.4 | 80 | 80 | 79 | 88 | 90 | 90 | 91 | 83 | 76 | 83 | 88 | 0 | 0 | 0 | 0 | 0 |
| b-IL5.5 | 81 | 84 | 83 | 90 | 92 | 93 | 93 | 87 | 79 | 86 | 90 | 0 | 0 | 0 | 0 | 0 |
| b-IL5.6 | 77 | 80 | 79 | 87 | 90 | 90 | 90 | 81 | 75 | 81 | 84 | 0 | 0 | 0 | 0 | 0 |
| b-IL5.7 | 86 | 88 | 86 | 93 | 94 | 94 | 94 | 88 | 85 | 90 | 94 | 0 | 0 | 0 | 0 | 0 |
| b-IL5.8 | 94 | 95 | 93 | 98 | 94 | 97 | 98 | 95 | 93 | 95 | 97 | 0 | 0 | 0 | 0 | 0 |
| b-IL5.9 | 94 | 95 | 94 | 98 | 98 | 98 | 98 | 95 | 95 | 96 | 98 | 0 | 0 | 0 | 0 | 0 |
| b-IL5.10 | 72 | 74 | 74 | 75 | 74 | 74 | 75 | 76 | 70 | 85 | 79 | 0 | 0 | 0 | 0 | 0 |
| b-IL5.11 | 73 | 75 | 72 | 86 | 87 | 88 | 87 | 78 | 68 | 79 | 84 | 0 | 0 | 0 | 0 | 0 |
| b-IL5.12 | 0 | 0 | 0 | 0 | 0 | 0 | 0 | 0 | 0 | 0 | 0 | 97 | 88 | 85 | 91 | 78 |
| b-IL5.13 | 0 | 0 | 0 | 0 | 0 | 0 | 0 | 0 | 0 | 0 | 0 | 96 | 96 | 96 | 96 | 83 |
| b-IL5.14 | 0 | 0 | 0 | 0 | 0 | 0 | 0 | 0 | 0 | 0 | 0 | 96 | 95 | 96 | 96 | 82 |
| b-IL5.15 | 0 | 0 | 0 | 0 | 0 | 0 | 0 | 0 | 0 | 0 | 0 | 96 | 94 | 96 | 96 | 81 |
| b-TRFK-5 | 0 | 0 | 0 | 0 | 0 | 0 | 0 | 0 | 0 | 0 | 0 | 88 | 85 | 86 | 87 | 94 |

Values represent percent inhibition of maximum b-mAb signal by a hundred fold excess of competing mAb.
Maximum signal is defined as that generated by a given b-mAb in the absence of competing mAb.
Values in bold indicate inhibition of each b-mAb by unlabeled self.

IL-5 mediated eosinophila in both mice and guinea pigs (Bloom, J. W., et al., *J. Immunol.* 151:2707 (1993); Coffman, R. L., et al., *Science* 245:308 (1989); Rennick, D. M., et al., *Blood* 76:312 (1990); Owen, W. F., et al., *J. Exp. Med.* 170:343 (1989); Chand, N., et al., *Eur. J. Pharm.* 211:121 (1991)), suggests that analogous therapy with anti-hIL-5 mAb might be feasible in blocking IL-5 mediated inflammation in humans.

In sum, specificity to hIL-5 was assessed by direct ELISA. All mAb bound only rhIL-5. No binding was detected with baculovirus expressed mIL-5 indicating that anti-hIL-5 mAb binding was not specific to Sf9 cell glycosylation of the rhIL-5. By competitive ELISA, all mAb could be divided between two binding groups, A and B (Table II). Group A consisted of eleven mAb and group B consisted of four mAb which competed for TRFK-5 binding to hIL-5. No further distinction could be made within a given group, as competition could be a result of epitope identify or merely steric interference between a given pair of mAb within each group. However since TRFK-5 is capable of binding mIL-5 (Table I), its epitope cannot be the same as any recognized by any group B mAb. Thus competition for binding between TRFK-5 and group B mAb must be a result of steric hinderance. Therefore, at least three epitopes have been demonstrated for hIL-5, all of which are neutralizing.

EXAMPLE 5

BCL$_1$ PROLIFERATION ASSAY

All mAb were screened for their ability to neutralize rhIL-5 (1 µg/ml) and rmIL-5 (1 ng/ml) biological activity in a BCL$_1$ proliferation assay with a constant concentration of IL-5 (FIG. 1).

For this purpose, 25 µl of rhIL-5 (1 µg/ml final concentration) or rmIL-5 (1) ng/ml final concentration) were preincubated with 25 µl of each mAb, a positive control mAb, TRFK-5, or an irrelevant isotype matched mAb (OKT11), all at a final concentration of 20 µg/ml, or with media only for one hour at 37° C. Fifty microliters of BCL$_1$ cells (4×10$^5$ cells/ml) in RPMI media, 10% FCS, 2 mM L-glutamine, 50 µg/ml 2-ME, 15 mM HEPES, and 50 µg/ml gentamicin were added and incubate for 16 hours at 37° C. in 5% CO$_2$ humidified air. After 16 hours, 1 µCi of [$^3$H] thymidine (Amersham Buckinghamshire, England) was added per well and incubated for another 8 hours. At 24 hours the cells were harvested and [$^3$H]thymidine incorporation measured by a liquid scintillation counter (Beckman, Pala Alto, Calif.).

To assess the dose dependency of anti-hIL-5 mAb neutralization, mAb were titrated against a constant concentration of rhIL-5. Twenty five microliters of rhIL-5 (1 µg/ml final concentration) in RPMI complete media were incubated with 25 µl of each anti-hIL-5 mAb, TRFK-5 (positive control), and anti-OK11 mAb (negative control) (2–0.005 µg/ml 2 fold dilutions) plus a media control for one hour at 37° C. Addition of BCL$_1$ cells, labeling, and harvesting were the same as described above.

Figure 2:
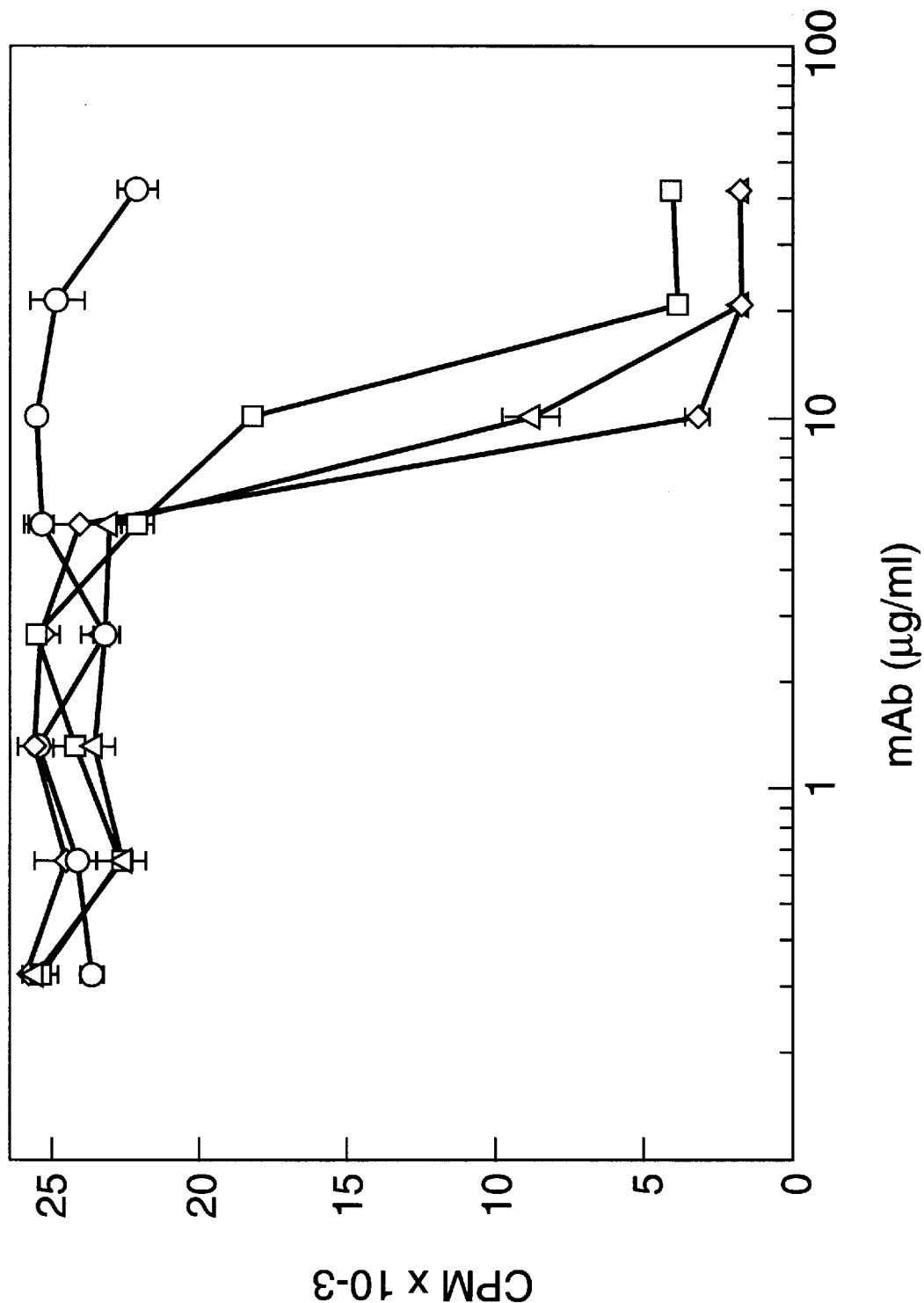
FIG. 2 shows the dose dependency of mAb neutralization of rhIL-5. IL5.7, a group A mAb representative (open square), IL5.15, a group B mAb representative (open triangle), TRFK-5, a positive control mAb for neutralization (open diamond), and anti-OKT11, an irrelevant isotype matched mAb (open circle) were titrated in serial two fold dilutions starting with 40 μg/ml and incubated with 1 μg/ms rhIL-5. All other mAb not shown yielded similar results. Samples were assayed in triplicate and data are expressed as the mean ±SE.

In comparison to the media control (no mAb), TRFK-5 served as a positive control for neutralization. TRFK-5 was capable of neutralizing biological activity of both rhIL-5 and rmIL-5. An irrelevant isotype matched mAb (murine IgG$^1$, kappa), anti-OKT11 had no significant effect on either rhIL-5 or rmIL-5. All murine mAb significantly neutralized rhIL-5, with group B mAb having more neutralizing potential at 20 µg/ml than group A mAb. None of these antibodies however had any significant effect on rmIL-5. Neutralization by all mAb were shown to be dose dependent. FIG. 2 demonstrates this dependency for IL5.7 and IL5.15, representatives of group A and group B mAb respectively, and TRFK-5. Maximum neutralization of 1 µg/ml of rhIL-5 was achieved with 20 µg/ml of both mAb as well as TRFK-5. Neutralization diminished to zero for all mAb at 5 µg/ml. The isotype-matched control mAb, anti-OKT11, had no effect of rhIL-5 activity over the entire range of MAb concentrations.

EXAMPLE 6

WESTERN BLOT ANALYSIS

To assess potential conformational requirements for epitope recognition by each mAb, Western analyses of both reduced and nonreduced rhIL-5 were conducted using each mAb as the primary detecting antibody.

Thus, recombinant hIL-5 was diluted to approximately 15 ng/lane and electrophoresed through a 12% polyacrylamide SDS gel under either reducing or nonreducing conditions. For each gel a Rainbow molecular weight markers (Amersham, Arlington Height, Ill.) lane was run to monitor electrophoresis and efficiency of transfer. Protein was transferred to a PVDF immobilon-P membrane (Millipore, Bedford, Mass.) in a Trans-Blot Cell (BioRad, Hercules, Calif.) 500 mA for two hours at 15° C. Membranes were blocked with PBS 0.05% tween 0.5% nonfat dry milk O.N. at 4° C. Membranes were then assembled in a Miniblotter 16 (Immunetics, Cambridge, Mass.). Each mAb was diluted to 100 µg/ml in blocker and 150 µl added to the appropriate lane and incubated for one hour at room temperature. Membranes were developed using an Enhanced Chemiluminescence (ECL) Western blotting kit and Hyperfilm-MP (Amersham, Arlington Height, Ill.). Between each step membranes were wash three time with PBS 0.05% tween 0.5% BSA for 10 min on a shaker with a final PBS 0.5% tween rinse.

Figure 3A:
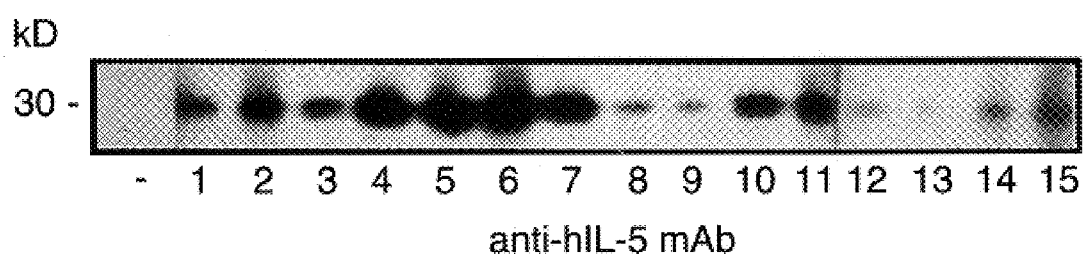
FIGS. 3A–3B show western analysis of reduced and nonreduced rhIL-5.
Figure 3B:
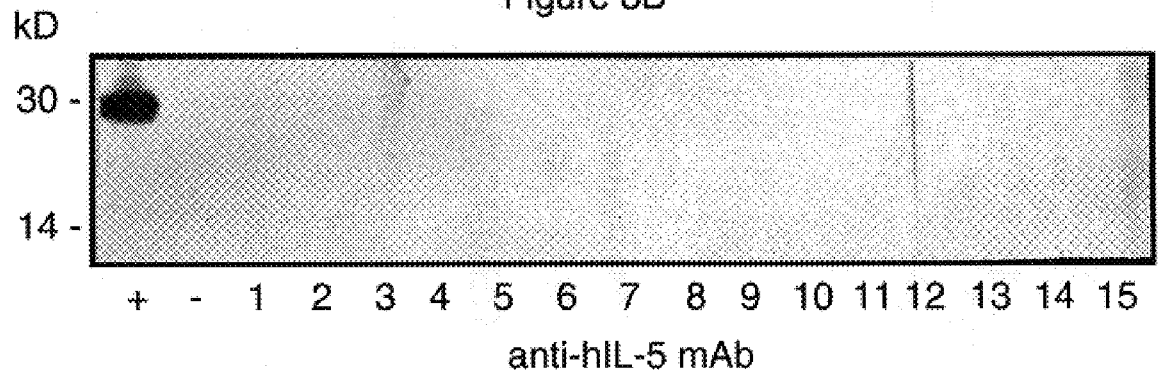

All mAb were found to bind denatured nonreduced rhIL-5, however to varying degrees (FIG. 3A). The mAb could be grouped based on intensity of the ECL signal (in decreasing order) IL5.4–7, IL5.1–3,10–11, IL5.8–9, and IL5.12–15. No mAb was bound denatured reduced rhIL-5.

Western analysis thus provides a means of further dividing the mAb groupings. By qualifying the intensity of signal from a normalized concentration of mAb and a fixed amount of hIL-5, four levels of relative intensity were defined (FIG. 3A). All group B mAb demonstrated poor binding by Western and thus could not be further subdivided. However, the group A mAb demonstrated three different degrees of intensity and thus could be subdivided by this characteristic. These differences may be due to multiple epitopes or merely to affinity differences to recognition of different epitopes or merely differences in affinity to the same epitope. What can be concluded is that all epitopes have some conformational dependency, since no mAb were found to bind reduced hIL-5, even at a levels as high as one microgram (data not shown). Therefore all mAb binding is dependent on at least one of the hIL-5 disulfide linkages. Finally ELISA combinations IL5.7:b-IL5.7 (group A), IL5.15:b-IL5.15 (group B), and TRFK-5:b-TRFK-5 were all capable of detecting hIL-5 (FIG. 4), demonstrating that each of these three classes of neutralizing epitopes must be present as a conformationally identical pair on the hIL-5 dimer.

Further analysis of other mAb combinations provides insight into the relative location of each epitope pair. The TRFK-5:b-TRFK-5 and the IL5.15:b-IL5.15 combinations were orders of magnitude less sensitive than the IL5.7:b-IL5.7 sandwich ELISA. This suggests that both group A epitopes are more available to simultaneous binding than those for a given group B mAb or TRFK-5. The less sensitive group B or TRFK-5 sandwich ELISA argues that having one of a given epitope bound by the capture mAb limits the availability for binding of the detecting b-mAb. This general conclusion that the group B and TRFK-5 epitopes are in closer proximity than the group A epitopes is further supported by ELISA which utilized unlike pairs. The IL5.7:b-1L5.15 pair improved sensitivity over the IL5.7:B-IL5.7 combination, suggesting that perhaps even partial restriction on the second group A epitope exists. Capturing with a group A mAb leaves one group B domain virtually free to bind to the respective detecting b-mAb. The fact that the IL5.7:b-TRFK-5 sandwich was less sensitive than the IL5.7:b-IL5.15 suggests that capturing with a group A mAb limits the TRFK-5 epitope more than that of group B. This further supports the conclusion that TRFK-5 and group B epitopes must be different. The most sensitivity combination and thus the combination suggesting the best detection epitope availability is the IL5.15:b-IL5.7 combination. Capture with IL5.15 resulted in the availability of nearly two other A epitopes, the most of any combination.

In summary, utilizing sensitive mAb combinations, highly sensitive and specific hIL-5 ELISA were developed. The sensitivity for the IL5.15:b-IL5.7 sandwich ELISA was 15 pg hIL-5/ml, which rivals other reported ELISA (K. C. Allison, et al., *J. Immunol.* 146:4197 (1991); McNamee, L. A., et al., *J. Immunol. Meth.* 141:81 (1991); Fukuda, Y., et al., *J. Immunol. Meth.* 143–89 (1991)) and is capable of detecting hIL-5 in biological fluids. At the same time this assay proved to be very specific, as undiluted sera and concentrated BAL samples from normal controls generated no detectable signal.

EXAMPLE 7

DEVELOPMENT OF AN hIL-5 SANDWICH ELISA

Figure 4:
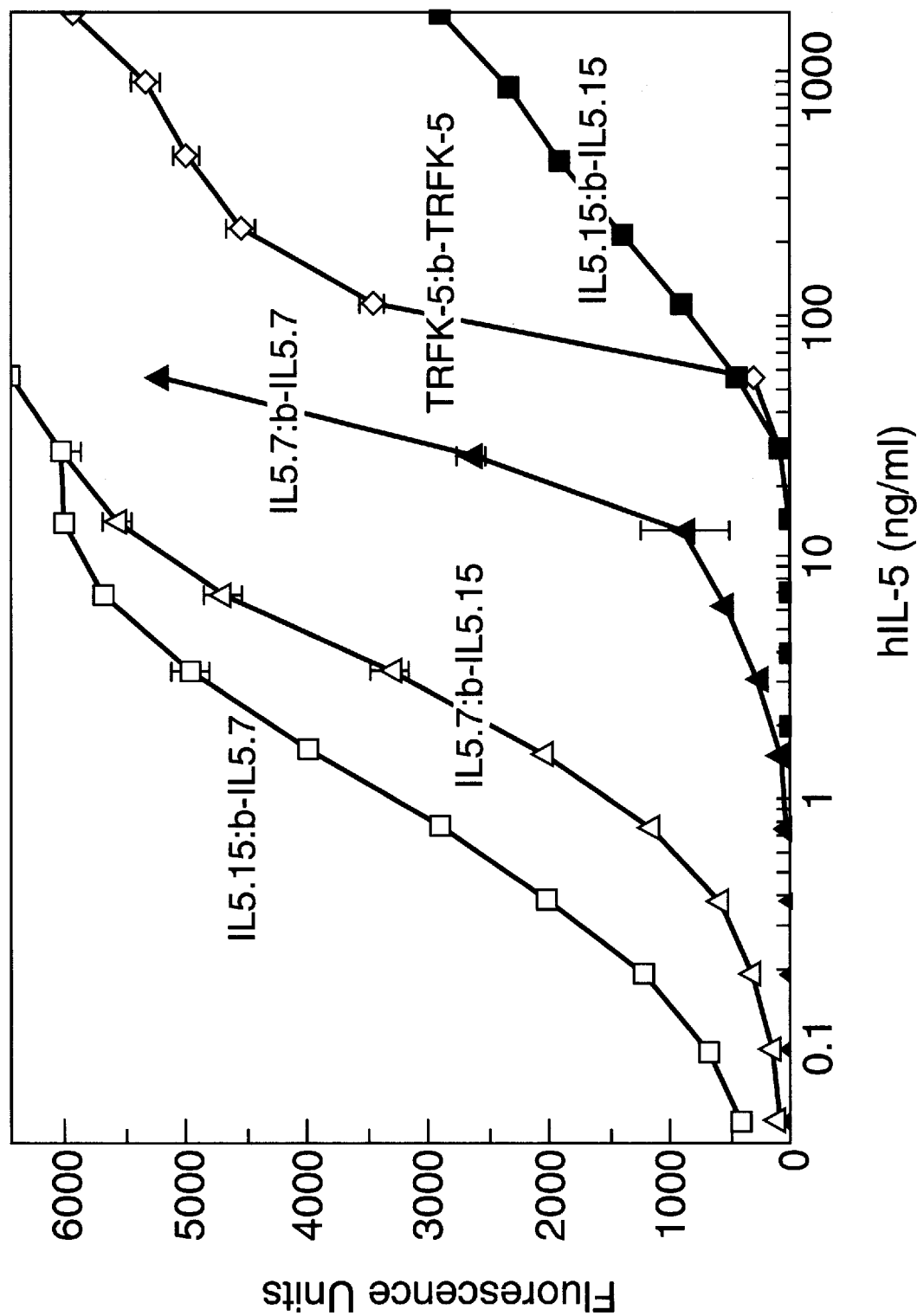
FIG. 4 shows the results of a human IL-5 sandwich ELISA. Plates were coated with either IL5.7, IL5.15 or TRFK-5 (5 μg/ml). Serial two fold dilutions of rhIL-5 starting with 50 ng/ml or 2 μg/ml were incubated in blocked wells. Biotinylated mAb, b-IL5.7, b-IL5.15, or b-TRFK-5 were used for detection. Samples were assayed in triplicate with data expressed as the mean ±SE.
Figure 5:
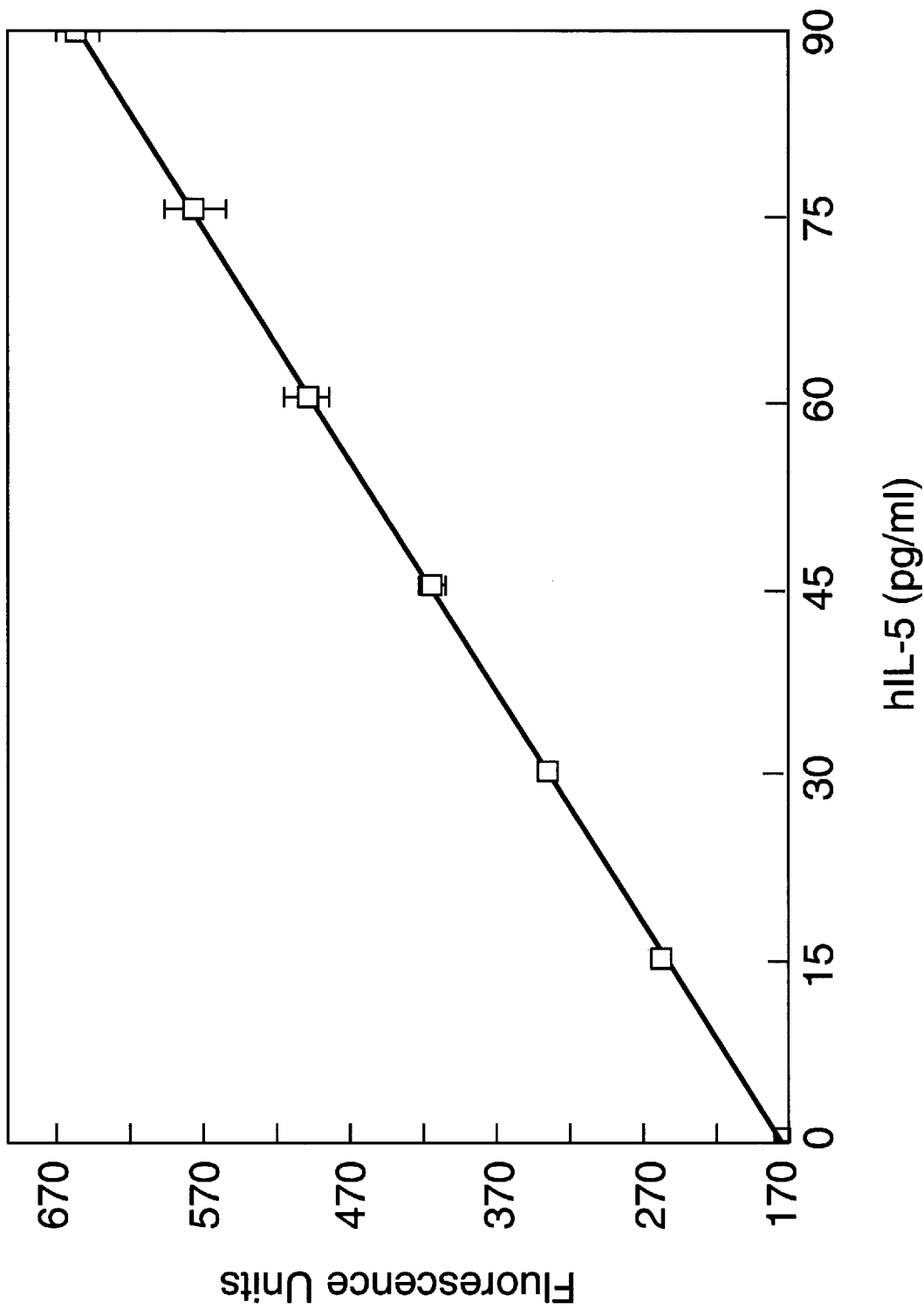
FIG. 5 shows the sensitivity of the hIL-5 sandwich ELISA. Plates were coated with IL5.15 and detected with b-IL5.7. Dilutions of rhIL-5 between 90 and 15 pg/ml were assayed in triplicate. Data are expressed as the mean of three experiments ±SE. Significance between points as established using the Tukey test (P<0.01).

In an attempt to develop a highly specific and sensitive hIL-5 ELISA, various combinations of capture mAb and detection b-mAb were employed (FIG. 4).

Thus, polystyrene ELISA plates (Corning, Corning, N.Y.) were coated with 50 µl of a given capture mAb (5 µg/ml in PBS) and incubated overnight at 4° C. Plates were blocked with PBS 0.5% tween 10% calf serum. Fifty microliters of standard dilutions of affinity purified rhIL-5 (in triplicate) and dilutions of blinded samples (in triplicate) were incubated. Sera samples were run without further processing, while bronchoalveolar (BAL) fluid was concentrated 20 times in an Amicon protein concentrator using a 10 kD cut-off filter. Biotinylated mAb (1/500) were used for detection of bound hIL-5. The strepavidin-alkaline phosphatase/MUP system described above was used to develop the assay. Unless otherwise specified, all incubation were for one hour at room temperature and between incubations plates were washed five times with PBS 0.05% tween.

Serum was collected from a patient with eosinophilic pneumonia. BAL fluid was collected from a patient with acute lung rejection. All other samples were from normal individuals.

The previously described TFFK-5:b-TRFK-5 sandwich was again demonstrated to have a relatively poor sensitivity on the order of tens of ng/ml. The combination of IL5.15:b-IL5.15 (group B representative) proved just as insensitive and had a lower signal throughout is usable range when compared to the TRFK-5:b-TRFK-5 ELISA. The combination of IL5.7:b-IL5.7 (group A representative) was slightly more sensitive approaching a lower limit of 1 ng/ml. Further enhancement of sensitivity was achieved using IL5.7 as the capture antibody and detecting with b-IL5.15 (lower limit approaching 100 pg/ml). However the best combination with the greatest sensitivity was achieved using the IL5.15:b-IL5.7 sandwich whose lower detection limit was 15 pg/ml (P<0.01). This sensitivity could not be improved with a cocktail of all b-mAb. Sera from a patient with eosinophilic pneumonia and thirteen normal controls were assayed for hIL-5 (Table III). Although no hIL-5 was detected in any of his normal control samples, hIL-5 was measurable in the serum of the hypereosinophilic patient (Table III). In addition, a 20-fold concentration BAL from a patient undergoing lung transplant rejection contained measurable quantities of hIL-5, whereas hIL-5 was not detected in similarly concentrated BAL from a healthy control individual (Table III). In Table III, BAL fluid was concentrated 20 times; all samples were assayed in triplicate, and reported values are the mean ±SE. Control sera values represent th mean of 13 independent samples; a zero indicates the absence of a signal over background.

TABLE III

Detection of hIL-5 in Biological Fluids

| Sample | hIL-5 (pg/ml) |
|---|---|
| Eosinophilic Serum | 2083 ± 112 |
| Control Sera | 0 |
| Inflammatory BAL | 174 ± 9 |
| Control BAL | 0 |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A murine monoclonal antibody selected from the group consisting of IL5.1–IL5.15 and fragments thereof, wherein said antibody or fragment:

(A) specifically binds to human interleukin-5;

(B) substantially fails to bind to murine interleukin-5; and (C) in the presence of human interleukin-5 and a second murine monoclonal antibody selected from the group consisting of IL5.1-IL5.15, forms a detectable molecular complex that comprises said antibody, said interleukin-5, and said second murine monoclonal antibody.

2. The murine monoclonal antibody according to claim 1, wherein the monoclonal antibody is IL5.1 or a fragment thereof.

3. The murine monoclonal antibody according to claim 1, wherein the monoclonal antibody is IL5.2 or a fragment thereof.

4. The murine monoclonal antibody according to claim 1, wherein the monoclonal antibody is IL5.3 or a fragment thereof.

5. The murine monoclonal antibody according to claim 1, wherein the monoclonal antibody is IL5.4 or a fragment thereof.

6. The murine monoclonal antibody according to claim 1, wherein the monoclonal antibody is IL5.5 or a fragment thereof.

7. The murine monoclonal antibody according to claim 1, wherein the monoclonal antibody is IL5.6 or a fragment thereof.

8. The murine monoclonal antibody according to claim 1, wherein the monoclonal antibody is IL5.7 or a fragment thereof.

9. The murine monoclonal antibody according to claim 1, wherein the monoclonal antibody is IL5.8 or a fragment thereof.

10. The murine monoclonal antibody according to claim 1, wherein the monoclonal antibody is IL5.9 or a fragment thereof.

11. The murine monoclonal antibody according to claim 1, wherein the monoclonal antibody is IL5.10 or a fragment thereof.

12. The murine monoclonal antibody according to claim 1, wherein the monoclonal antibody is IL5.11 or a fragment thereof.

13. The murine monoclonal antibody according to claim 1, wherein the monoclonal antibody is IL5.12 or a fragment thereof.

14. The murine monoclonal antibody according to claim 1, wherein the monoclonal antibody is IL5.13 or a fragment thereof.

15. The murine monoclonal antibody according to claim 1, wherein the monoclonal antibody is IL5.14 or a fragment thereof.

16. The murine monoclonal antibody according to claim 1, wherein the monoclonal antibody is IL5.15 or a fragment thereof.

17. A murine hybridoma cell line that produces a monoclonal antibody selected from the group consisting monoclonal antibodies IL5.1-IL5.15, wherein said monoclonal antibody:

(A) specifically binds to human interleukin-5;

(B) substantially fails to bind to murine interleukin-5; and (C) in the presence of human interleukin-5 and a second murine monoclonal antibody selected from the group consisting of IL5.1-IL5.15, forms a detectable molecular complex that comprises said antibody, said interleukin-5, and said second murine monoclonal antibody.

18. The murine hybridoma cell line according to claim 17, wherein the hybridoma produces monoclonal antibody IL5.1.

19. The murine hybridoma cell line according to claim 17, wherein the hybridoma produces monoclonal antibody IL5.2.

20. The murine hybridoma cell line according to claim 17, wherein the hybridoma produces monoclonal antibody IL5.3.

21. The murine hybridoma cell line according to claim 17, wherein the hybridoma produces monoclonal antibody IL5.4.

22. The murine hybridoma cell line according to claim 17, wherein the hybridoma produces monoclonal antibody IL5.5.

23. The murine hybridoma cell line according to claim 17, wherein the hybridoma produces monoclonal antibody IL5.6.

24. The murine hybridoma cell line according to claim 17, wherein the hybridoma produces monoclonal antibody IL5.7.

25. The murine hybridoma cell line according to claim 17, wherein the hybridoma produces monoclonal antibody IL5.8.

26. The murine hybridoma cell line according to claim 17, wherein the hybridoma produces monoclonal antibody IL5.9.

27. The murine hybridoma cell line according to claim 17, wherein the hybridoma produces monoclonal antibody IL5.10.

28. The murine hybridoma cell line according to claim 17, wherein the hybridoma produces monoclonal antibody IL5.11.

29. The murine hybridoma cell line according to claim 17, wherein the hybridoma produces monoclonal antibody IL5.12.

30. The murine hybridoma cell line according to claim 17, wherein the hybridoma produces monoclonal antibody IL5.13.

31. The murine hybridoma cell line according to claim 17, wherein the hybridoma produces monoclonal antibody IL5.14.

32. The murine hybridoma cell line according to claim 17, wherein the hybridoma produces monoclonal antibody IL5.15.

33. A method for the detection of human IL-5 in a sample, comprising the steps:

(1) contacting said sample with a first monoclonal antibody selected from the group consisting of IL5.1–IL5.15 and fragments thereof, wherein said antibody or fragment:

specifically binds to human interleukin-5;

substantially fails to bind to murine interleukin-5; and in the presence of human interleukin-5 and a second murine monoclonal antibody selected from the group consisting of IL5.1–IL5.15, forms a detectable molecular complex that comprises said first antibody, said interleukin-5, and said second murine monoclonal antibody, under conditions that permit formation of a complex between the first monoclonal antibody and human IL-5;

(2) contacting said complex with a second monoclonal antibody selected from the group consisting of IL5.1–IL5.15 and fragments thereof under conditions insufficient to permit formation of a complex comprising IL-5 and both monoclonal antibodies; and (3) determining a level of any complex formed comprising IL-5 and both monoclonal antibodies;

wherein the level of the complex containing both monoclonal antibodies and IL-5 is correlated to the concentration of IL-5 in the sample.

34. The method of claim 33, wherein the first monoclonal antibody is selected from the group consisting of IL5.15 and fragments of IL5.15, and the second monoclonal antibody is selected from the group consisting of IL5.7 and fragments of IL5.7.

35. The method of claim 34, wherein the concentration of IL-5 in the sample is equal to or greater than 15 pg/mL.

* * * * *